United States Patent [19]

Chernoff

[11] Patent Number: 4,852,559
[45] Date of Patent: Aug. 1, 1989

[54] DEVICE FOR PINNING BONE FRACTURES

[76] Inventor: Ira Chernoff, 515 E. 72 St., Apt. 19A, New York, N.Y. 10021

[21] Appl. No.: 184,312

[22] Filed: Apr. 21, 1988

[51] Int. Cl.$^4$ ............................................. A61F 5/04
[52] U.S. Cl. ............................................. 128/92 YZ
[58] Field of Search ........ 128/92 YD, 92 YE, 92 YF, 128/92 YK, 92 YP, 92 YY, 92 YZ, 92 ZZ; 411/485, 923, 487

[56] References Cited

U.S. PATENT DOCUMENTS

| | | | |
|---|---|---|---|
| 498,890 | 6/1893 | Taylor | 411/485 |
| 2,235,419 | 3/1941 | Callahan et al. | 128/92 YK |
| 2,314,481 | 3/1943 | Crooks | 411/485 |
| 3,279,300 | 10/1966 | Larson | 411/485 |
| 3,513,747 | 5/1970 | Dirks | 411/487 |
| 3,997,138 | 12/1976 | Crock et al. | 128/92 YF |
| 4,275,490 | 6/1981 | Bivins | 128/92 YR |
| 4,409,970 | 10/1983 | Carrel | 128/92 YF |

FOREIGN PATENT DOCUMENTS

| | | | |
|---|---|---|---|
| 238605 | 6/1964 | Austria | 411/485 |
| 1040188 | 8/1966 | United Kingdom | 411/485 |

*Primary Examiner*—Robert A. Hafer
*Assistant Examiner*—Charles H. Sam
*Attorney, Agent, or Firm*—Sprung, Horn, Kramer & Woods

[57] ABSTRACT

A device for pinning bone fractures includes an integral metal pin having an elongated shaft and a head at one end of the pin comprising an arcuate hook having an inner radial surface and an outer radial surface and a closed loop formed at the inner radial surface of the hook.

7 Claims, 1 Drawing Sheet

DEVICE FOR PINNING BONE FRACTURES

BACKGROUND OF THE INVENTION

The present invention relates to a device for pinning bone fractures.

Devices of this type are known and one particular commercial version of the device is known as the "rush" pin manufactured by the Rush/Berivon, Inc. Co. Meridianm, Miss.

These pins are pre-bent elongated metal pins having an elongated shaft ending in a point and a head at one end which includes an open hook.

In use, a hole is drilled in the fractured bone to be set and the pin is inserted therein by a mallet or similar device until fully inserted.

Recently, the pinning technique has been used in conjunction with a tension band technique wherein a figure-eight shaped band is held in place at one loop with the heads of two pins and the other loop is placed through a hole in the bone in order to provide dynamic compression on the fracture.

One disadvantage of these two combined techniques is that the tension on the band has tended to force the pins outwardly from the bone, which is undesirable since it requires the pins to be reimplanted or removed by the doctor if the fracture is healed.

SUMMARY OF THE INVENTION

The main object of the present invention is to eliminate the disadvantages of the prior art devices and to provide a device for pinning bone fractures which is particularly useful in conjunction with the tension band technique.

These and other objects and advantages of the present invention are achieved in accordance with the present invention by a device comprising an integral metal pin having an elongated shaft and a head at one end of the pin comprising an arcuate hook having an inner radial surface and an outer radial surface and means forming a closed loop at the inner radial surface of the hook.

In an advantageous embodiment of the present invention, the means forming the closed loop includes the inner radial surface of the hook.

In another embodiment of the present invention, the elongated shaft of the pin has indicia therealong for indicating the length of the shaft from the head end of the pin. This enables the user to cut the pin prior to insertion after the length of the hole drilled in the bone has been determined.

These and other features of the present invention will be seen from the following detailed description of the invention taken with the attached drawings, wherein:

DETAILED DESCRIPTION OF THE INVENTION

Figure 1:
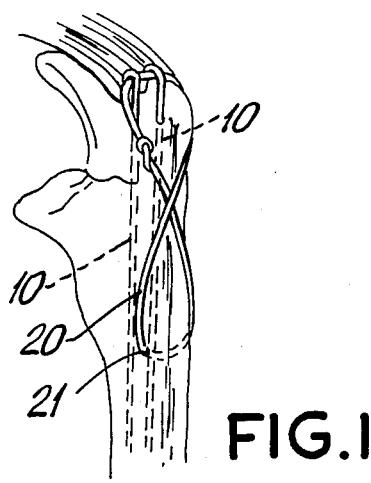
FIG. 1 shows pins inserted into a fractured bone and a tension band.

FIG. 1 shows the pin 10 inserted into a broken bone and the utilization of the tension band 20 therewith.

As can be seen, the pins are inserted through drilled holes in the bones and the length of insertion of the drill itself can be used to measure the available hole for the pin. The band 20 is then placed through a hole 21 in the bone distal to the fracture to provide dynamic tension.

Figure 2:
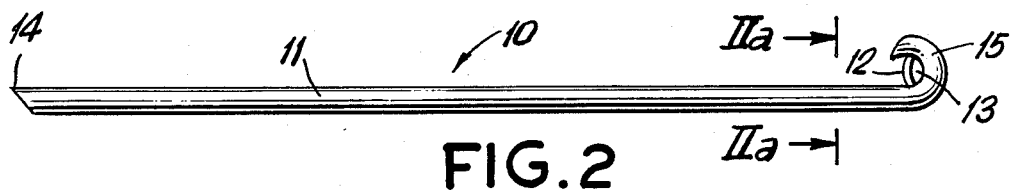
FIG. 2 is a side view of a pinning device according to the present invention.
Figure 2A:
FIG. 2a is a sectional view of FIG. 2 along line IIa—IIa.

Pin 10 is shown in more detail in FIG. 2 and FIG. 2a and includes a shaft 11 having a pointed end 14 and a head at the other end including an arcuate hook 15 and means forming a closed loop 13 including metal segment 12 connected to the inner radial surface of the hook 15 and forming the closed loop 13 with the inner radial surface of hook 15.

In use, the band 20 is threaded through hole 13 in both pins and member 12 prevents movement of the pin 10 outwardly from the bone when in the position shown in FIG. 1.

The width of the element 12 is preferably substantially narrower than that of the pin 10 which has a virtually constant diameter throughout so as to enable the head 15 to be inserted as far as possible into the bone. Since the bone tissue is soft, the relatively narrow element 12 will embed therein.

In FIG. 2 the element 12 is convex at its outermost surface.

Figure 3:
FIG. 3 is a side view of another pinning device according to the present invention.

In the embodiment shown in FIG. 3, the element 32 which forms the hole 33 with hook 15 is concave in its outer surface. Moreover, the shaft portion 11' of the pin has indicia 17a–17e therealong which indicates the length of the shaft from the head 15.

Figure 4:
FIG. 4 is a partial view of a further embodiment of the pinning device according to the present invention.
Figure 4A:
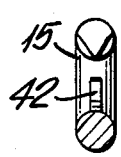
FIG. 4a is a sectional view along line IVa—IVa in FIG. 4.

FIG. 4 illustrates another embodiment of the device according to the present invention wherein element 42 is utilized to form closed loop 43. A front view of element 42 is shown in FIG. 4a.

Figure 5:
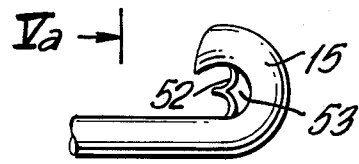
FIG. 5 is a partial view of still another embodiment according to the present invention.
Figure 5A:
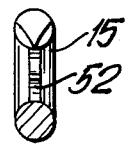
FIG. 5a is a sectional view along line Va—Va in FIG. 5.

Similarly in FIGS. 5 and 5a, loop 53 is formed by member 52 which has a pointed front end and thus can be more easily inserted into the bone.

Figure 6:
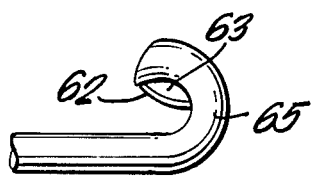
FIG. 6 is a partial view of a still further embodiment according to the present invention.

FIG. 6 shows a further embodiment wherein hook 65 has a member 62 at the free end forming loop 63.

It will be appreciated that the instant specification and claims are set forth by way of illustration and not limitation, and that various modifications and changes may be made without departing from the spirit and scope of the present invention.

What is claimed is:

1. A device for pinning bone fractures, comprising: an integral metal pin having an elongated shaft and a head at one end of the pin, said head comprising an arcuate hook having a free end, an inner radial surface and an outer radial surface, and means extending from said shaft to said inner radial surface and forming a closed loop with the inner radial surface of the hook, said closed loop not extending past the free end of the arcuate hook.

2. The device according to claim 1, wherein the means forming the closed loop includes the inner radial surface of the hook.

3. The device according to claim 1, wherein the other end of the pin has a point thereon.

4. The device according to claim 1, further comprising indicia at a plurality of locations along the shaft for indicating the length of the shaft from the one end of the pin.

5. The device according to claim 1, wherein the shaft has a smooth unobstructed surface.

6. The device according to claim 5, wherein the hook and the shaft have the same cross section with no obstruction therebetween.

7. The device according to claim 1, wherein the shaft and head are J-shaped and the closed loop is entirely contained within the hook of the J-shape.

* * * * *